(12) United States Patent
Isaacson et al.

(10) Patent No.: US 12,420,013 B2
(45) Date of Patent: Sep. 23, 2025

(54) IV FLOW MANAGEMENT SYSTEMS AND METHODS

(71) Applicant: Becton, Dickinson and Company, Franklin Lakes, NJ (US)

(72) Inventors: S. Ray Isaacson, Layton, UT (US); Weston F. Harding, Lehi, UT (US); Ralph L. Sonderegger, Farmington, UT (US); Austin Jason McKinnon, Herriman, UT (US); Milan Ivosevic, Kinnelon, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 279 days.

(21) Appl. No.: 18/119,650

(22) Filed: Mar. 9, 2023

(65) Prior Publication Data

US 2023/0211079 A1 Jul. 6, 2023

Related U.S. Application Data

(62) Division of application No. 16/854,648, filed on Apr. 21, 2020, now Pat. No. 11,617,831, which is a
(Continued)

(51) Int. Cl.
*A61M 5/172* (2006.01)
*A61M 5/168* (2006.01)
(Continued)

(52) U.S. Cl.
CPC ........ *A61M 5/172* (2013.01); *A61M 5/16813* (2013.01); *A61M 5/16877* (2013.01);
(Continued)

(58) Field of Classification Search
None
See application file for complete search history.

(56) References Cited

U.S. PATENT DOCUMENTS 4,372,304 A * 2/1983 Avakian ............ A61M 5/16813
251/8
4,634,426 A * 1/1987 Kamen ............... A61M 5/1689
128/DIG. 13
(Continued)

FOREIGN PATENT DOCUMENTS

JP 4863591 9/1973
JP 61206445 9/1986

OTHER PUBLICATIONS

Gale Encyclopedia of Nursing and Allied Health_Intravenous Fluid Regulation_Encyclopedia.com (Year: 2006).*

*Primary Examiner* — Manuel A Mendez
(74) *Attorney, Agent, or Firm* — Kirton McConkie; Whitney Blair; Erik Ence

(57) ABSTRACT

An intravenous delivery system may operate by gravity feed, and may have a liquid source containing a liquid, a drip unit that receives the liquid from the liquid source, and tubing that receives the liquid from the drip unit for delivery to a patient. A flow rate sensor may be used to measure a flow rate of liquid through the intravenous delivery system, and may generate a flow rate signal indicative of the flow rate. A controller may receive the signal, and may compare the flow rate with a desired flow rate. If the flow rate is more or less than the desired flow rate, the controller may transmit a control signal to a flow rate regulator. The flow rate regulator may receive the control signal and, in response, modify the flow rate to bring the flow rate closer to the desired flow rate.

16 Claims, 5 Drawing Sheets

Related U.S. Application Data division of application No. 15/078,727, filed on Mar. 23, 2016, now Pat. No. 10,646,648.

(60) Provisional application No. 62/141,398, filed on Apr. 1, 2015.

(51) Int. Cl.
*A61M 5/14* (2006.01)
*A61M 5/38* (2006.01)
*A61M 39/20* (2006.01)

(52) U.S. Cl.
CPC .... *A61M 5/16881* (2013.01); *A61M 5/16895* (2013.01); *A61M 5/1411* (2013.01); *A61M 5/16845* (2013.01); *A61M 5/1689* (2013.01); *A61M 5/385* (2013.01); *A61M 2039/205* (2013.01); *A61M 2205/3331* (2013.01); *A61M 2205/3368* (2013.01); *A61M 2205/3379* (2013.01); *A61M 2205/502* (2013.01); *A61M 2205/7536* (2013.01)

(56) References Cited

U.S. PATENT DOCUMENTS

| | | | | |
|---|---|---|---|---|
| 4,681,563 | A * | 7/1987 | Deckert | A61M 5/1689 |
| | | | | 128/DIG. 13 |
| 4,820,281 | A * | 4/1989 | Lawler, Jr. | A61M 5/1689 |
| | | | | D24/129 |
| 5,503,225 | A | 4/1996 | Withers | |
| 6,685,668 | B1 * | 2/2004 | Cho | A61M 5/172 |
| | | | | 604/118 |
| 7,255,680 | B1 * | 8/2007 | Gharib | A61M 5/16859 |
| | | | | 604/67 |
| 9,435,455 | B2 * | 9/2016 | Peret | A61M 39/281 |
| 10,646,648 | B2 * | 5/2020 | Isaacson | A61M 5/16895 |
| 2009/0093774 | A1 * | 4/2009 | Wang | A61M 5/16881 |
| | | | | 604/247 |
| 2016/0339229 | A1 * | 11/2016 | Hung | A61M 39/281 |

\* cited by examiner

IV FLOW MANAGEMENT SYSTEMS AND METHODS

RELATED APPLICATIONS

This application is a divisional of U.S. patent application Ser. No. 16/854,648, filed Apr. 21, 2020, and entitled IV FLOW MANAGEMENT SYSTEMS AND METHODS, which is a divisional of U.S. patent application Ser. No. 15/078,727, filed Mar. 23, 2016, and entitled IV FLOW MANAGEMENT SYSTEMS AND METHODS, which claims the benefit of U.S. Provisional Patent Application No. 62/141,398, filed Apr. 1, 2015, and entitled IV FLOW MANAGEMENT SYSTEMS AND METHODS, which are incorporated herein in their entirety.

BACKGROUND

The present invention is generally directed to systems and methods for intravenous ("IV") delivery, by which fluids can be administered directly to a patient. More particularly, the present invention is directed systems and methods for monitoring and/or managing the flow of a liquid to a patient in the context of a gravity-fed intravenous delivery system. An intravenous delivery system according to the invention is used broadly herein to describe components used to deliver the fluid to the patient, for use in arterial, intravenous, intravascular, peritoneal, and/or non-vascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip unit with a drip chamber used to moderate the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

Such intravenous delivery systems often function via "gravity feed." In a gravity feed system, the liquid source may be elevated above the patient, so that a "head" or pressure differential exists between the liquid in the liquid source, and the location at which the liquid is delivered to the patient. The pressure differential may enable pumps or other fluid transfer mechanisms to be eliminated, thereby reducing the cost and bulk of the intravenous delivery system.

Unfortunately, many such intravenous delivery systems have difficulties maintaining a constant flow of the liquid to the patient. The level of the liquid in the liquid source will recede over time, and the patient may move, resulting in variations in the pressure differential that determines the flow rate of the liquid. Additionally, tubing and/or other components of the intravenous delivery system may become pinched, blocked, or otherwise occluded, resulting in unexpected changes in the flow rate of the liquid.

Currently, clinicians often measure the flow rate of the liquid by counting the drops entering the drip chamber over a set period of time. The clinician must then calculate the resulting flow rate and compare it to the desired flow rate to determine the necessary flow rate adjustment. This flow rate adjustment may then be made by manually adjusting a device such as a clamp on the tubing. The clinician may then count the drops entering the drip chamber again to determine whether the desired flow rate has been achieved. This procedure is time-consuming for the clinician, and subject to human error.

Accordingly, a less time-consuming and more reliable method is needed for controlling the flow rate of liquid delivered via an intravenous delivery system. Further, in order to reduce the cost of medical care delivery, there exists a need for such methods to be simple and cost-effective, and preferably to avoid the necessity for complicated equipment.

BRIEF SUMMARY OF THE INVENTION

Embodiments of the present invention are generally directed to systems and methods for controlling the flow rate of liquid through an intravenous delivery system. The intravenous delivery system may have a liquid source containing a liquid to be delivered to a patient, a drip unit, and tubing. The tubing may have a first end connectable to the liquid source, and a second end connectable to a vent cap and/or an intravenous delivery unit that provides the liquid intravenously to the patient.

The intravenous delivery system may have a flow rate control system that controls the flow rate of the liquid to the patient. The flow rate control system may have a flow rate sensor, a flow rate regulator, and a controller. The flow rate sensor may detect the flow rate of the liquid flowing through the intravenous delivery system and transmit a flow rate signal indicative of the flow rate to the controller. The controller may compare the flow rate to a desired flow rate, and if needed, transmit a control signal to the flow rate regulator to cause the flow rate regulator to move to a different state, in which a larger or smaller flow rate of the liquid is provided.

The flow rate sensor may be coupled to the drip unit to measure the rate at which the liquid flows through the drip unit. This may be accomplished by counting the drops of the liquid that enter the drip chamber within a predetermined period of time, measuring the differential mass of the liquid over a predetermined period of time, measuring the differential volume of the liquid over a predetermined period of time, measuring a difference in liquid temperature upstream and downstream of a heat source, and/or through the use of other methods.

In one embodiment, the flow rate sensor may have an interior cavity that receives the lower portion of the drip unit, with arms that extend upward toward the top of the drip unit. One arm may have a light source, and the other arm may have a light sensor that detects the light from the light source. Drops of the liquid entering the drip chamber may block the light, and may thus be detected and counted through the use of the light sensor. The flow rate sensor may have a key feature receiver that receives a key feature on the drip unit to provide information pertinent to the drip unit to the flow rate sensor, such as the size of the orifice through which drops of the liquid enter the drip chamber. Thus, the number of drops may be counted to determine the flow rate of the liquid into the drip chamber.

The flow rate regulator may be coupled to the tubing to control the rate of liquid flow through the tubing by compressing the tubing to varying degrees. The flow regulator may have a pinching member that slides along a slot oriented at an angle relative to the tubing, such that the pinching member pinches the tubing closed at the end of the slot that is nearest to the tubing, and allows the tubing to be completely open at the end of the slot that is furthest from the tubing. Alternatively, the flow rate regulator may have a cam member with a variable radius curved rim that rotates to different orientations to variably pinch the tubing between the variable radius curved rim and an opposing member.

The flow rate sensor may transmit a flow rate signal indicative of the flow rate to the controller. The controller may compare the flow rate with the desired flow rate, and may a control signal to the flow rate regulator, if needed. The flow rate signal and the control signal may be sent and received via wired and/or wireless transmission. The controller may have a user input device and a display screen that facilitates receipt of data from a user such as a clinician, and facilitates display of other information, such as the flow rate, to the clinician.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
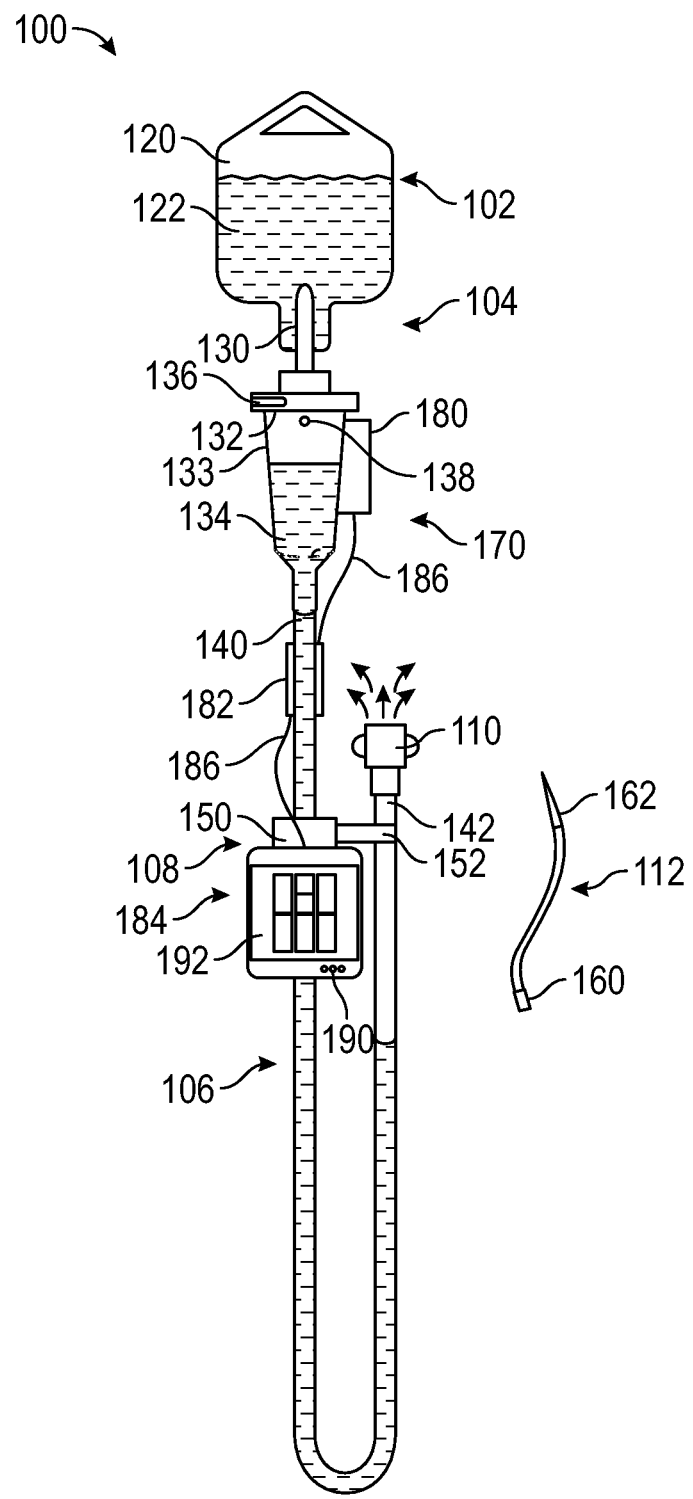
FIG. 1 is a front elevation view of an intravenous delivery system with a flow rate control system according to one embodiment.

Referring to FIG. 1, a front elevation view illustrates an intravenous delivery system 100 according to one embodiment. As shown, the intravenous delivery system 100 may have a number of components, which may include a liquid source 102, a drip unit 104, tubing 106 a retention unit 108, a vent cap 110, and an intravenous access unit 112. The manner in which these components are illustrated in FIG. 1 is merely exemplary; those of skill in the art will recognize that a wide variety of intravenous delivery systems exist. Thus, the various components the intravenous delivery system 100 may be omitted, replaced, and/or supplemented with components different from those illustrated.

The liquid source 102 may have a container containing a liquid 122 to be delivered intravenously to a patient. The liquid source 102 may, for example, have a membrane 120, which may be formed of a translucent, flexible polymer or the like. The membrane 120 may thus have a baglike configuration. The membrane 120 may be shaped to contain the liquid 122.

The drip unit 104 may be designed to receive the liquid 122 from the membrane 120 in a measured rate, for example, as a series of drips occurring at a predictable, consistent rate. The drip unit 104 may be positioned below the membrane 120 so as to receive the liquid 122 via gravity feed. The drip unit 104 may have a receiving device 130 that receives the liquid 122 from the liquid source 102, a drip feature 132 that determines the rate at which the liquid 122 is received by the drip unit 104, and an exterior wall 133 that defines a drip chamber 134 in which the liquid 122 is collected. The drip feature 132 may have an orifice 136 through which the liquid 122 passes to reach the drip chamber 134; the size (for example, diameter) of the orifice 136 may determine the size of the drops 138, and hence, the volume of the liquid 122 in each of the drops 138.

The tubing 106 may be standard medical grade tubing. The tubing 106 may be formed of a flexible, translucent material such as a silicone rubber. The tubing 106 may have a first end 140 and a second end 142. The first end 140 may be coupled to the drip unit 104, and the second end 142 may be coupled to the vent cap 110, such that the liquid 122 flows from the drip unit 104 to the vent cap 110, through the tubing 106.

The retention unit 108 may be used to retain various other components of the intravenous delivery system 100. As shown, the retention unit 108 may have a main body 150 and an extension 152. Generally, the tubing 106 may be connected to the main body 150 proximate the first end 140, and to the extension 152 proximate the second end 142. Various racks, brackets, and/or other features may be used in addition to or in place of the retention unit 108.

The vent cap 110 may be coupled to the second end 142 of the tubing 106. The vent cap 110 may have a vent, such as a hydrophilic membrane that is substantially permeable to air, but not to the liquid 122. Thus, air from within the vent cap 110 can be vented from the intravenous delivery system 100, with limited leakage of the liquid 122 from the intravenous delivery system 100.

The intravenous access unit 112 may be used to supply the liquid 122 to the vascular system of the patient. The intravenous access unit 112 may have a first end 160 and an access end 162 with a cannula or other feature configured to deliver the liquid 122 internally to the patient. The first end 160 may be connectable to the second end 142 of the tubing 106 in place of the vent cap 110. Thus, when the intravenous delivery system 100 is fully primed, the intravenous access unit 112 may be coupled to the second end 142 of the tubing 106 in place of the vent cap 110. In alternative embodiments (not shown), various connectors such as Y-adapters may be used to connect the first end 160 of the intravenous access unit 112 to the tubing 106 without detaching the vent cap 110 from the second end 142 of the tubing 106.

The intravenous delivery system 100 may be primed by connecting the components (except for the intravenous access unit 112) together as illustrated in FIG. 1, and then allowing the liquid 122 to gravity feed through the drip unit 104 and the tubing 106 into the vent cap 110. If desired, the drip unit 104 may be squeezed or otherwise pressurized to expedite flow of the liquid 122 through the tubing 106.

As the liquid 122 flows through the tubing 106, air may become entrained in the liquid 122. This air may move from the first end 140 of the tubing 106, toward the second end 142 of the tubing 106, along with the column of liquid 122. This entrained air may gather into bubbles proximate the second end 142 of the tubing 106. The vent cap 110 may be designed to receive the liquid 122 to permit such air bubbles to be vented from the intravenous delivery system 100 through the vent cap 110. Once air has been vented from within the intravenous delivery system 100, the intravenous access unit 112 may be coupled to the second end 142 of the tubing 106 and used to deliver the liquid 122 to the patient.

The intravenous delivery system 100 may also include a flow rate control system 170 that monitors and controls the flow rate of the liquid 122 to the patient. The flow rate control system 170 may have a flow rate sensor 180, a flow rate regulator 182, and a controller 184. The flow rate sensor 180, the flow rate regulator 182, and the controller 184 may be connected together in a manner that permits signals to pass between them, for example, via wires 186.

The flow rate sensor 180 may sense the flow rate of the liquid 122 passing through the drip unit 104, and transmit a flow rate signal to the controller 184 indicative of the flow rate. The controller 184 may determine whether the flow rate is too large or too small, and may transmit a corresponding control signal to the flow rate regulator 182. The flow rate regulator 182 may then operate to reduce or increase the flow rate of the liquid 122 through the intravenous delivery system 100. This method will be show and described in greater detail in connection with FIG. 2.

The flow rate sensor 180 is shown in generalized form, and may thus have a variety of configurations. As shown, the flow rate sensor 180 may be secured to the drip unit 104 to measure the flow rate of the liquid 122 through the drip unit 104. In alternative embodiments, the flow rate sensor 180 may be secured to and/or positioned proximate other components, such as the liquid source 102, the tubing 106, the retention unit 108, and/or the intravenous access unit 112, in order to measure the flow rate of the liquid 122 through those components.

The flow rate sensor 180 may include any of a wide variety of sensor types. According to some embodiments, the flow rate sensor 180 may function by counting the number of drops 138 received within the drip chamber 134 within a predetermined period of time, in a manner similar to that followed by clinicians when manually assessing flow rates of existing intravenous delivery systems. For example, the flow rate sensor 180 may have a light source (not shown) and an optical sensor (not shown) positioned on opposite sides of the drip unit 104. The optical sensor may detect occlusion of the light source due to the existence of the one of the drops 138 between the optical sensor and the light source, and may thus register the presence of the drop 138. The flow rate sensor 180 may increment a count each time a new occlusion is measured to count the number of the drops 138. One example of such a flow rate sensor 180 will be shown and described in connection with FIG. 3.

As another exemplary embodiment in which the flow rate sensor 180 counts the drops 138, electrodes (not shown) may be positioned in the interior of the drip chamber 134 such that each drop 138 completes and electrical circuit to indicate the presence of the drop 138. The flow rate sensor 180 may count the number of times the circuit is closed to count the number of the drops 138. Other exemplary methods of counting the drops 138 include the use of an acoustic sensor (not shown) within the drip chamber 134 to count the number of times a drop 138 strikes the liquid 122 within the drip chamber 134 based on the resulting acoustic energy, and the use of a floater (not shown) with an accelerometer or other motion sensor (not shown) that detects the resulting ripples to count the drops 138.

In other embodiments, the flow rate sensor 180 may measure different values to determine the flow rate of the liquid 122 through the intravenous delivery system 100. For example, a scale (not shown) may be used to measure the weight of one or more components of the intravenous delivery system 100. For example, the liquid source 102 may hang from a hook or other implement (not shown) connected to a strain gauge-based load cell or the like (not shown) to measure the weight of the liquid source 102, the drip unit 104, and/or the portion of the tubing 106 that is supported by the hook. Weight measurements may be taken before and after a predetermined time period. The differential weight may be the weight of the liquid 122 that has flowed from the hanging components to the patient during the predetermined period of time. If desired, the liquid 122 to be administered to the patient may be gravimetrically prepared so that the desired flow rate (by weight) of the liquid 122 will be known.

In still other embodiments, the flow rate sensor 180 may measure changes in the volume of the liquid 122 to determine the flow rate of the liquid 122 through the intravenous delivery system 100. For example, the volume of the liquid 122 remaining in the liquid source 102 may be measured before and after passage of a predetermined period of time. The differential volume may be the volume of the liquid 122 that has flowed through the intravenous delivery system 100 during the predetermined period of time. Volume may be measured, for example, by measuring the pressure of the liquid 122 in the bottom of the liquid source 102 with a pressure sensor (not shown) or the like. The pressure of the liquid 122 within the liquid source 102 may provide the height of the column of the liquid 122 (above the pressure sensor), and this, in combination with the horizontal cross-sectional area of the liquid source 102 may be used to obtain the volume of the liquid 122 within the liquid source 102.

The volume of the liquid 122 may additionally or alternatively be measured by measuring the height of the liquid 122 within the liquid source 102 through the use of electrodes (not shown) in the wall of the liquid source 102. Inductance and/or capacitance between electrodes may be measured to determine the height of the column of the liquid 122. Again, the horizontal cross-sectional area of the liquid source 102 may be used, in combination with the change in height of the column of the liquid 122, to ascertain the volume of the liquid 122 that has flowed through the intravenous delivery system 100. The resolution of height measurements that can be made via this method may be limited to the spacing between adjacent electrodes. The accuracy of the measurement may be enhanced by using many electrodes and positioning them close together, and/or selecting a longer predetermined time period for measurement.

In yet other embodiments, the flow rate sensor 180 may measure still other aspects of the liquid 122. For example, the flow rate sensor 180 may include a heat source (not shown) such as a resistive heater, and two temperature sensors (not shown) such as thermocouples, which may be positioned upstream and downstream of the heat source. The temperature differential between the two temperature sensors may be proportional to the flow rate of the liquid, as more rapid flow may expedite heat transfer by convection from the heat source to the downstream temperature sensor. Some such flow rate sensors are marketed by Sensirion, AG of Switzerland. The temperature sensors and heat source may beneficially be positioned in a relatively narrow fluid pathway, such as that of the bottom portion of the drip unit 104 and/or the tubing 106, so as to minimize turbulence and other factors that may otherwise cause unpredictable flow of the heat from the heat source.

These are just some examples of flow rate sensors that may be used within the scope of the present disclosure. A wide variety of sensors and methods are known for detection of liquid flow rates; those of skill in the art will recognize that a flow rate control system, such as the flow rate control system 170, may utilize any known sensor and method.

The flow rate regulator 182 is also shown in generalized form and may also have a variety of configurations. The flow rate regulator 182 may be coupled to the tubing 106 between the first end 140 and the second end 142. If desired, the flow rate regulator 182 may act as a valve, and may only have an open state that permits relatively free flow of the liquid 122 through the intravenous delivery system 100, and a closed state in which such flow is not permitted. Additionally or alternatively, the flow rate regulator 182 may have multiple open states that provide varying rates of flow (for example, a more open state and a less open state). The flow rate regulator 182 may have only a limited number of discrete states, or may provide continuous adjustability between two end states, such as a fully open state and a fully closed state.

The flow rate regulator 182 may include any of a wide variety of regulator types. According to some embodiments, the flow rate regulator 182 may function by applying a variable degree of pinching force to the tubing 106, thereby providing adjustability in the flow rate of the liquid 122 through the tubing 106. Examples of such embodiments will be shown and described with reference to FIGS. 4 and 5.

In other embodiments, the flow rate regulator 182 may regulate the flow rate of the liquid 122 through the intravenous delivery system 100 through the use of other structures and/or methods. For example, the flow rate regulator 182 may include a valve (not shown), which may have a valve seat and a plunger that resides in the valve seat in the closed state, but permits the liquid 122 to flow between the valve seat and the plunger in the open state. Such a valve may have multiple open states that provide varying flow rates, for example, based on the amount of space through which the liquid 122 can flow between the plunger and the valve seat. A wide variety of valves exist, including but not limited to ball valves, butterfly valves, ceramic disc valves, choke valves, diaphragm valves, gate valves, globe valves, knife valves, needle valves, pinch valves, piston valves, plug valves, poppet valves, and spool valves. The flow rate regulator 182 may, in various embodiments, incorporate any one or more such valve designs.

These are just some examples of flow rate regulators that may be used within the scope of the present disclosure. A wide variety of sensors and methods are known for regulation of liquid flow rates; those of skill in the art will recognize that a flow rate control system, such as the flow rate control system 170, may utilize any known regulator and method.

The controller 184 is illustrated in FIG. 1 in a more particular embodiment. As shown, the controller 184 may be secured to the retention unit 108 for easy access. The controller 184 may be integrated in a computing device having a tablet-like design, with a user input device 190 and a display screen 192. The user input device 190 may include various buttons and/or switches. The display screen 192 may utilize any of various display technologies, and may display information for the clinician, in textual and/or graphical form, that pertains to the operation of the intravenous delivery system 100. If desired, the display screen 192 may be a touch screen or the like, and may thus also act as a user input device.

The controller 184 may be coupled to the flow rate sensor 180 and the flow rate regulator 182 via the wires 186. Thus, the controller 184 may receive flow rate signals from the flow rate sensor 180 indicative of the flow rate of the liquid 122, and may transmit control signals to the flow rate regulator 182 that indicate how the flow rate of the liquid 122 is to be modified. The controller 184 may also have a processor capable of receiving the flow rate signals, performing any computational steps needed to ascertain which control signals should be sent, and generating the control signals for transmission to the flow rate regulator 182.

The controller 184 may optionally be used for functions besides the regulation of the flow of the liquid 122 through the intravenous delivery system 100. For example, the controller 184 may help to track the condition of the patient and/or other treatments administered to him or her. If desired, information from other monitors may be routed to the controller 184 and displayed on the display screen 192.

The controller 184 of FIG. 1 is merely exemplary. In other embodiments, a controller according to the present disclosure may be part of any type of computing device, including but not limited to desktop computers, computer terminals, tablets, PDA's smartphones, and the like. Thus, a controller may have various hardware and software components. A controller according to the present disclosure may be designed only for flow rate regulation, or may be a multi-function device.

Further, a controller according to the present disclosure may be housed in various structures. The controller 184 of FIG. 1 is in a housing independent from the flow rate sensor 180 and the flow rate regulator 182. However, in alternative embodiments (not shown), a controller may be integrated with either or both of a flow rate sensor and a flow rate regulator. Such a controller may be located in the same housing as the flow rate sensor or the flow rate regulator. If desired, all three components (flow rate sensor, flow rate regulator, and controller) may all share a common housing, which may, for example, be coupled to the drip unit 104 and to the tubing 106, adjacent to the drip unit 104.

Figure 2:
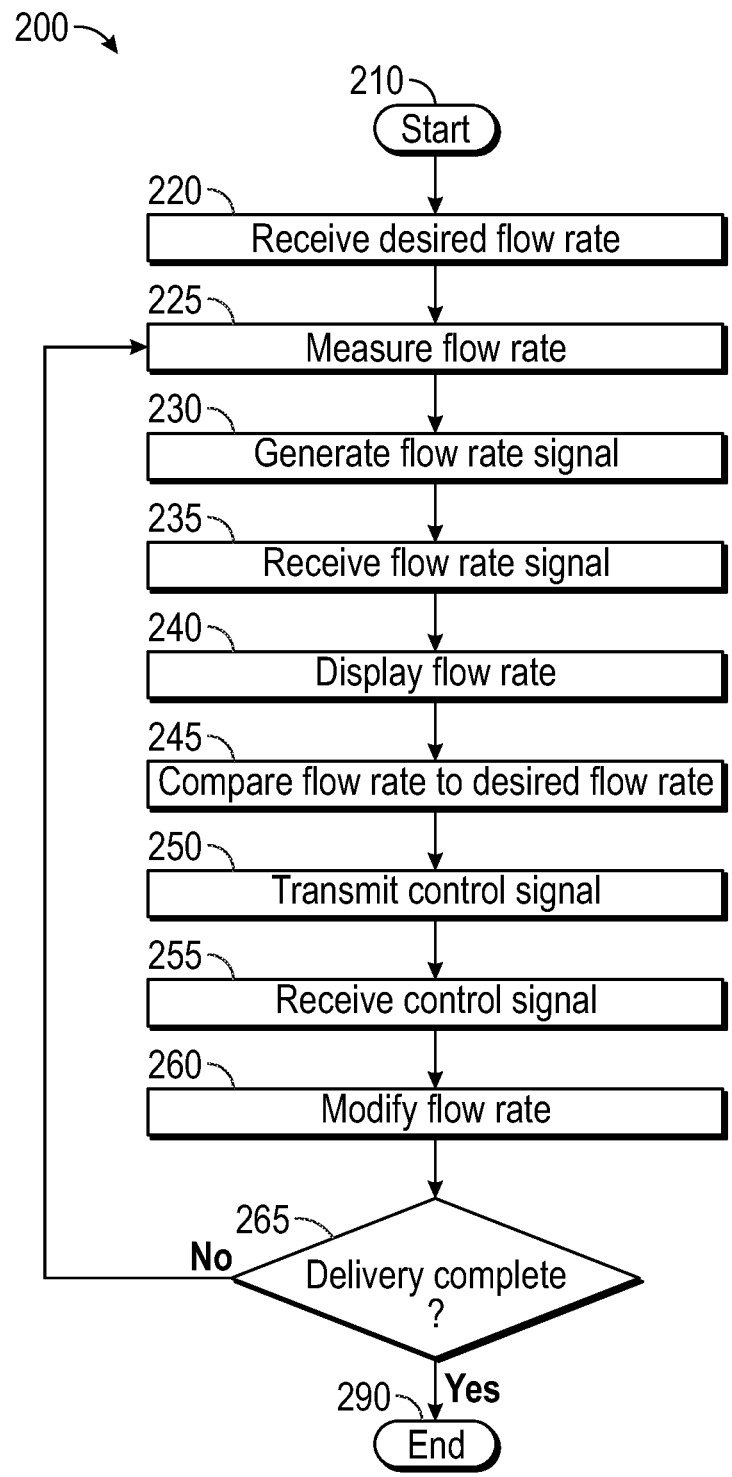
FIG. 2 is a flowchart diagram illustrating a method of controlling the flow rate of liquid delivered with an intravenous delivery system, according to one embodiment.

A method 200, in generalized form, of controlling the flow of the liquid 122 through the intravenous delivery system 100 will be provided in connection with FIG. 2. A more specific example will be presented in connection with FIG. 6.

Referring to FIG. 2, a flowchart diagram illustrates a method 200 of controlling the flow of an infusate through an intravenous delivery system, according to one embodiment. The method 200 will be described with reference to the intravenous delivery system 100 of FIG. 1, including the flow rate control system 170. However, those of skill in the art will recognize that the method 200 may be carried out with different intravenous delivery systems and/or different flow rate control systems. Similarly, the intravenous delivery system 100, including the flow rate control system 170, may be used via methods other than that of FIG. 2.

The method 200 may start 210 with a step 220 in which the desired flow rate is received, for example, by the controller 184. This may be done by permitting a user, such as a clinician, to enter the desired flow rate via the user input device 190 of the controller 184. The desired flow rate may be a specific volumetric or gravimetric flow rate, which may be an ideal flow rate about which some variation is acceptable. Additionally or alternatively, the desired flow rate may be a range of volumetric or gravimetric flow rates that are acceptable. If desired, the desired flow rate may be shown on the display screen 192 of the controller 184. The step 220 may be omitted if the desired flow rate is already present in the controller 184, for example, from a previous infusion.

In a step 225, the flow rate of the liquid 122 through the intravenous delivery system 100 may be measured by the flow rate sensor 180. This may be done in any of a wide variety of ways, as set forth in the description of FIG. 1. In a step 230, the flow rate sensor 180 may generate a flow rate signal indicative of the measured flow rate. The flow rate signal may be transmitted by the flow rate sensor 180.

In a step 235, the controller 184 may receive the flow rate signal. In a step 240, the controller 184 may optionally display the flow rate, for example, on the display screen 192 of the controller 184. Thus, a clinician may easily glance at the display screen 192 to view the desired flow rate and/or the current flow rate of the liquid 122 through the intravenous delivery system 100.

In a step 245, the flow rate measured by the flow rate sensor 180 may be compared with the desired flow rate. This may entail comparing the flow rate to a single desired flow rate, or to the upper and lower bounds of a range of desired flow rates. This comparison may simply entail subtracting the desired flow rate from the flow rate, yielding a flow rate differential indicative of (a) whether the flow rate is above or below the desired flow rate, and (b) the magnitude of the difference between the flow rate and the desired flow rate.

The controller 184 may generate a control signal indicative of the correction in flow rate that needs to be made. The control signal may specify whether to move the flow rate regulator 182 to an open state or a closed state, and/or the magnitude of flow that should be permitted through the flow rate regulator 182. In a step 250, the control signal may be transmitted by the controller 184.

In a step 255, the control signal may be received by the flow rate regulator 182. In a step 260, the flow rate regulator 182 may modify the flow rate of the liquid 122 through the intravenous delivery system 100 in accordance with the control signal. As indicated previously, this modification may entail moving the flow rate regulator 182 to a position in which all, part, or none of the flow of the liquid 122 is blocked by the flow rate regulator 182. In some embodiments, the control signal may direct the flow rate regulator 182 not to alter the flow rate at all. Additionally or alternatively, a control signal may be sent by the controller 184 only if there is to be a change in the flow rate of the liquid 122; in the event that the flow rate regulator 182 does not receive a flow rate signal at any given point in time, the flow rate regulator 182 may simply remain at the state corresponding to the last flow rate signal received.

In a query 265, the flow rate control system 170 (for example, in the controller 184) may determine whether delivery of the liquid 122 is complete. For example, if the flow rate sensor 180 detects that the liquid 122 is no longer flowing through the intravenous delivery system 100, and the flow rate regulator 182 is in an open state or a partially open state, the controller 184 may conclude that the liquid 122 has been depleted. Alternatively, a user such as a clinician may manually direct the controller 184 to stop infusion, for example, by entering a stop command on the user input device 190.

Additionally or alternatively, the controller 184 may be programmed to deliver a specific gravimetric or volumetric quantity of the liquid 122 to the patient. The controller 184 may maintain a record of the total volume and/or mass of the liquid 122 that has been delivered to the patient, and may increment this value as needed with every iteration. Once the specified amount of the liquid 122 has been delivered, the controller 184 may determine that infusion is complete, providing an affirmative answer to the query 265.

If the query 265 is answered in the affirmative, the method 200 may then end 290. If the query 265 is answered in the negative, additional quantities of the liquid 122 are to be delivered to the patient. Hence, the method 200 may proceed to a new iteration by returning to the step 225. Thus, the method 200 may iterate until infusion is complete and the method 200 ends 290.

Figure 3:
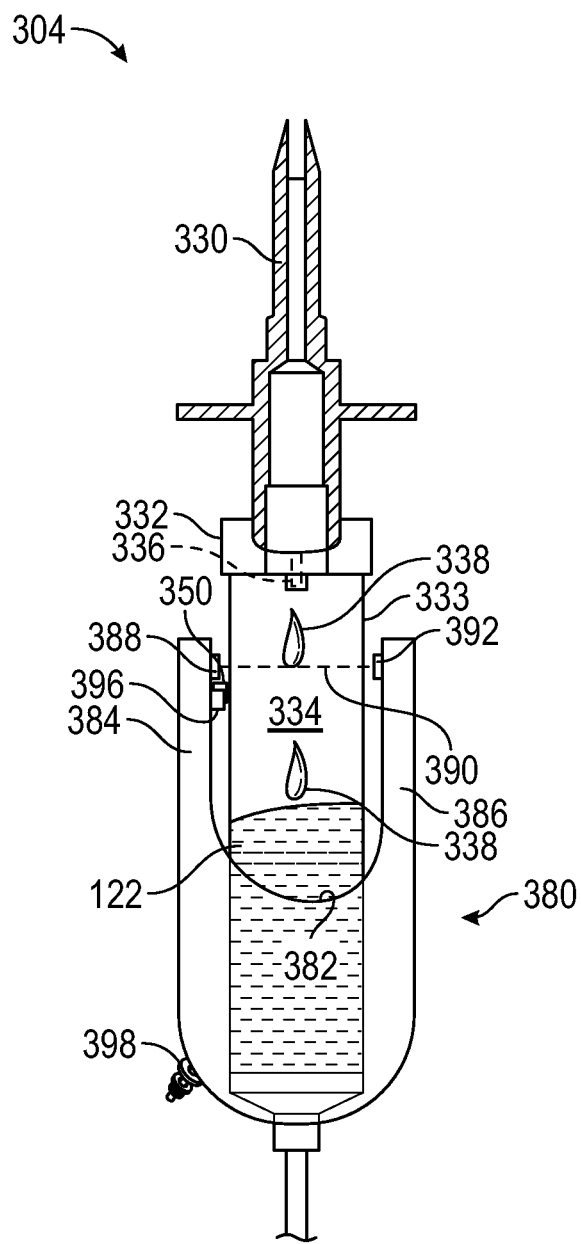
FIG. 3 is a front elevation view of a drip unit and flow rate sensor according to one embodiment.

Referring to FIG. 3, a front elevation view illustrates a drip unit 304 and flow rate sensor 380 according to one embodiment. The flow rate sensor 380 illustrates one manner in which the flow rate of the liquid 122 can be measured.

The drip unit 304 may be designed to receive the liquid 122 from a liquid source, such as the liquid source 102 of FIG. 1. The drip unit 304 may be positioned below the liquid source so as to receive the liquid 122 via gravity feed. The drip unit 304 may have a receiving device 330 that receives the liquid 122 from the liquid source, a drip feature 332 that determines the rate at which the liquid 122 is received by the drip unit 304, and an exterior wall 333 that defines a drip chamber 334 in which the liquid 122 is collected. The drip feature 332 may have an orifice 336 through which the liquid 122 passes to reach the drip chamber 334; the size (for example, diameter) of the orifice 336 may determine the size of the drops 338, and hence, the volume of the liquid 122 in each of the drops 338.

The drip unit 304 may have a key feature 350 that protrudes from the exterior wall 333 of the drip unit 304. The key feature 350 may be a ridge, polygonal protrusion, symbol, and/or any other feature. The key feature 350 may indicate the size of the orifice 336 to facilitate calculation of the flow rate of the liquid 122 by counting the number of the drops that enter the drip chamber 334. Generally, a "key feature" is any feature of an article that can be used to provide an indication of an attribute of a different feature of the article. In alternative embodiments (not shown), a drip chamber or other component of an intravenous delivery system may have a key feature that is a recess or other type of feature different from the feature types set forth above in connection with the key feature 350 of the drip unit 304.

The flow rate sensor 380 may be shaped to encase the lower portion of the drip unit 304, and may thus have an interior cavity 382 in which the drip unit 304 may be inserted. The flow rate sensor 380 may have a first arm 384 and a second arm 386 that extend upward toward the drip feature 332 of the drip unit 304.

The flow rate sensor 380 may be designed to count the number of the drops 338 that enter the drip chamber 334 optically, as described previously. Thus, the first arm 384 may have a light source 388, which may be a coherent light source such as a laser, or an incoherent light source. The light source 388 may emit light 390, which may pass through the drip chamber 334. The second arm 386 may have a light sensor 392 that detects the light 390. The light 390 may be of such a wavelength that the light 390 is absorbed, reflected, and/or refracted the liquid 122. Thus, the light 390 may be occluded when one of the drops 338 is present at the egress from the orifice 336, in alignment with the path followed by the light 390 as it travels from the light source 388 to the light sensor 392. Thus, the light sensor 392 may detect the formation of a drop 338 when the light 390 is no longer detected, and the release of the drop 338 when the light 390 is once again detected.

As indicated previously, the flow rate sensor 380 may count the number of times this cycle occurs within a predetermined period of time to determine how many of the drops 338 enter the drip chamber 334 within the predetermined period of time. The flow rate sensor 380 may have interior logic circuitry (not shown) capable of performing such calculations. The key feature 350 may provide the size of the orifice 336, which may be received by flow rate sensor 380 and used to determine the flow rate of the liquid 122 based on the number of drop 338 received within the drip chamber 334.

If desired, the flow rate sensor 380 may have a key feature receiver 396 that receives and/or otherwise registers with the key feature 350. The key feature receiver 396 may detect the configuration of the key feature 350 to enable the flow rate sensor 380 to determine the size of the orifice 336 based on the presence of the key feature 350. If desired, only one type of drip unit may have the key feature 350. In such an embodiment, the key feature receiver 396 need only detect whether or not the key feature 350 is present. The key feature receiver 396 need not differentiate between different types of key features. The key feature receiver 396 may thus have a switch, an electrical contact, or another element that can be used to electrically detect the presence of the key feature 350.

If desired, multiple different drip units may be made, with a variety orifice sizes and key feature types. Thus, the key feature receiver may be designed to determine not only that the key feature 350 is present, but also to determine which type of key feature 350 is on the drip unit 304. The key feature 350 may have one or more projecting fingers or other aspects that are detectable by the key feature receiver 396, for example, through the use of multiple switches, electrical contacts, or other elements (not shown) within the key feature receiver 396. Thus, the flow rate sensor 380 may automatically determine the size of the orifice 336 in response to assembly of the drip unit 304 and the flow rate sensor 380.

The flow rate sensor 380 may be connected to a controller (not shown), which may be similar to the controller 184 of FIG. 1, or may have a different configuration. If desired, the connection between the flow rate sensor 380 and the controller may be wireless. Thus, the flow rate sensor 380 may have a wireless transmitter 398 that wirelessly transmits the flow rate signal to the controller. The wireless transmitter 398 may operate based on any known wireless data transfer protocol, including but not limited to Wi-Fi, Bluetooth, Bluetooth Smart, ZigBee, NFC, and the like. The controller (not shown) may have a receiver capable of receiving the wireless signal transmitted by the flow rate sensor 380.

Figure 4:
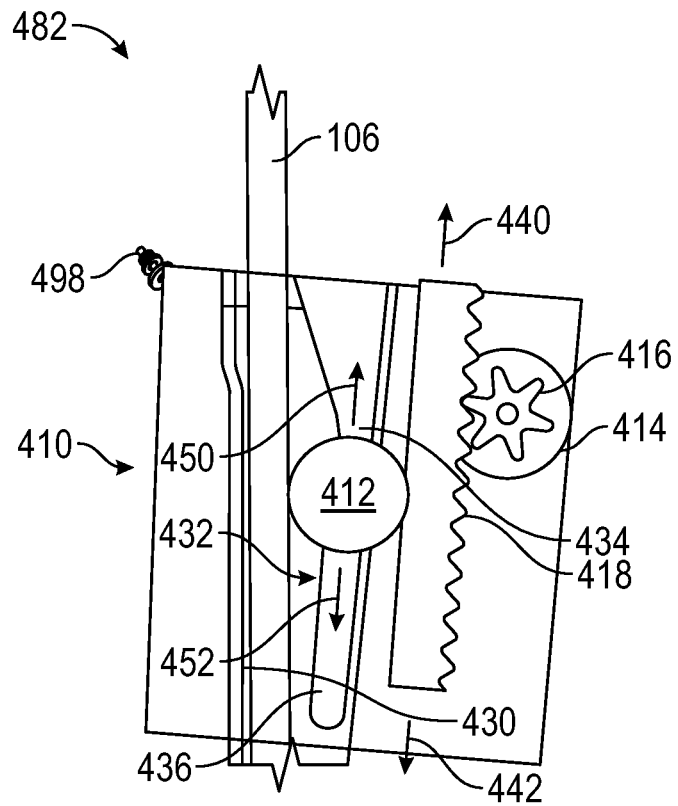
FIG. 4 is a front elevation, section view of a flow rate regulator according to one embodiment.

Referring to FIG. 4, a front elevation, section view illustrates a flow rate regulator 482 according to one embodiment. The flow rate regulator 482 may be coupled to the tubing 106 proximate the first end 140 of the tubing 106, like the flow rate regulator 182 of FIG. 1. The flow rate regulator 482 may be designed to control the flow rate of the liquid 122 through the intravenous delivery system 100 by pinching the tubing 106 to a variable degree.

The flow rate regulator 482 may have a frame 410, a pinching member 412, a motor 414, a pinion 416, and a rack 418. The frame 410 may secure the flow rate regulator 482 to the tubing 106. The frame 410 may be shaped to define an abutting surface 430 and a slot 432. The abutting surface 430 may extend alongside the tubing 106 such that the tubing 106 resides between the abutting surface 430 and the pinching member 412. The slot 432 may have a first end 434 and a second end 436.

The motor 414 may be secured to the frame 410, and the pinion 416 may be coupled to the motor 414 such that the pinion 416 rotates in response to rotation of the spindle of the motor 414. The rack 418 may be positioned between the pinion 416 and the pinching member 412 such that rotation of the pinion 416 causes the rack 418 to move in a first direction, as indicated by the arrow 440, or in a second direction, as indicated by the arrow 442. The pinching member 412 may have a shaft or other feature (not shown) that resides within the slot 432, and enables the pinching member 412 to move along the slot 432.

Motion of the rack 418 in the first direction may cause the pinching member 412 to move along the slot 432 in a first direction, as indicated by the arrow 450, toward the first end 434 of the slot 432. Similarly, motion of the rack 418 in the second direction may cause the pinching member 412 to move along the slot 432 in a second direction, as indicated by the arrow 452, toward the second end 436 of the slot 432. The pinching member 412 may be rigidly secured to the rack 418 such that the pinching member 412 translates along with the rack 418. Alternatively, the pinching member 412 may be rolled, in a combination of translation and rotation, by the motion of the rack 418. Rolling motion of the pinching member 412 may help to avoid undesired abrasion of the exterior surface of the tubing 106 by the pinching member 412 as the pinching member 412 moves along the slot 432.

The slot 432 may be oriented at an angle nonparallel and nonperpendicular to the tubing 106 and the abutting surface 430. The first end 434 of the slot 432 may be further from the tubing 106 and the abutting surface 430 than the second end 436 of the slot 432. Hence, motion of the pinching member 412 toward the first end 434 of the slot 432 may bring the pinching member 412 further from the abutting surface 430. This may causing the pinching member 412 and the abutting surface 430 to pinch less, or potentially not at all, on the tubing 106, thereby permitting a higher rate of flow of the liquid 122 through the tubing 106. On the other hand, motion of the pinching member 412 toward the second end 436 of the slot 432 may bring the pinching member 412 closer to the abutting surface 430. This may cause the pinching member 412 and the slot 432 to pinch more severely on the tubing 106, thereby reducing the flow rate of the liquid 122 through the tubing 106.

If desired, the pinching member 412 may be movable by degrees to various positions between the first end 434 and the second end 436 of the slot 432. Thus, the flow rate regulator 482 may provide multiple possible flow rates of the liquid 122. The motor 414 may be stepper motor or other motor that facilitates accurate positioning of the pinching member 412 by providing relatively precise motion stops. The pinching member 412 may additionally provide a fully open state when positioned proximate the first end 434, and a fully closed state when positioned proximate the second end 436. Thus, the flow rate regulator 482 may provide flexible flow rate control with a high degree of simplicity.

The flow rate regulator 482 may be connected to a controller (not shown), which may be similar to the controller 184 of FIG. 1, or may have a different configuration. If desired, the connection between the flow rate regulator 482 and the controller may be wireless. Thus, the flow rate regulator 482 may have a wireless receiver 498 that wirelessly receives the control signal from the controller. The wireless receiver 498 may operate based on any known wireless data transfer protocol, including but not limited to Wi-Fi, Bluetooth, Bluetooth Smart, ZigBee, NFC, and the like. The controller (not shown) may have a transmitter capable of sending the control signal wirelessly to the flow rate regulator 482.

Figure 5:
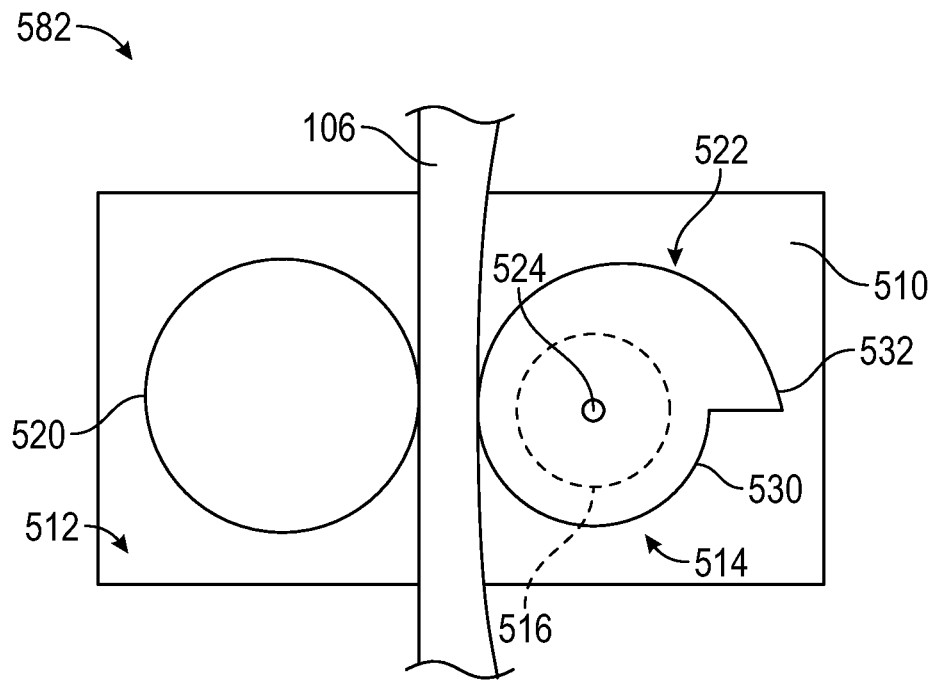
FIG. 5 is a front elevation view of a flow rate regulator according to another embodiment.

Referring to FIG. 5, a front elevation view illustrates a flow rate regulator 582 according to another embodiment. The flow rate regulator 582 may be coupled to the tubing 106 proximate the first end 140 of the tubing 106, like the flow rate regulator 182 of FIG. 1 and the flow rate regulator 482 of FIG. 4. The flow rate regulator 582 may be designed to control the flow rate of the liquid 122 through the intravenous delivery system 100 by pinching the tubing 106 to a variable degree.

The flow rate regulator 582 may have a frame 510, an opposing member 512, a cam member 514, and a motor 516. The frame 510 may secure the flow rate regulator 582 to the tubing 106, and may also support the opposing member 512, the cam member 514, and the motor 516. The opposing member 512 may have curved rim 520 that abuts the tubing 106. The opposing member 512 may be securely attached to the frame 510. The cam member 514 may have a variable radius curved rim 522 that also abuts the tubing 106. The cam member 514 may be rotatable relative to the frame 510 about an axis 524 through the use of the motor 516, which may be a stepper motor or other rotary motor that provides relatively accurate positional control.

The variable radius curved rim 522 of the cam member 514 may have a radius that increases relatively continuously along the variable radius curved rim 522, from a minimum diameter portion 530 to a maximum diameter portion 532. The minimum diameter portion 530 and the maximum diameter portion 532 may be adjacent to each other; thus, the variable radius curved rim 522 may have a discontinuity that separates the minimum diameter portion 530 from the maximum diameter portion 532.

When the motor 516 rotates to orient the cam member 514 with the minimum diameter portion 530 proximate the tubing 106, the cam member 514 and the opposing member 512 may cooperate to exert little or no pinching on the tubing 106, which may cause little or no restriction to flow of the liquid 122 through the tubing 106. Conversely, when the motor 516 rotates to orient the cam member 514 with the maximum diameter portion 532 proximate the tubing 106, the cam member 514 and the opposing member 512 may cooperate to exert maximum pinching on the tubing 106, which may cause the flow rate regulator 582 to be in a fully closed state.

When the motor 516 rotates to orient the cam member 514 with a portion of the variable radius curved rim 522 between the minimum diameter portion 530 and the maximum diameter portion 532 adjacent to the tubing 106, as shown in FIG. 5, the opposing member 512 and the cam member 514 may cooperate to exert a moderate level of pinching on the tubing 106, which is sufficient to slow, but not stop, flow of the liquid 122 through the tubing 106. The motor 516 may enable rotation of the cam member 514 to multiple orientations between the fully open and fully closed states, to permit fine tuning of the flow rate of the liquid 122 through the tubing 106. If desired, the variable radius curved rim 522 may have a relatively smooth surface that avoids catching and/or pulling on the exterior surface of the tubing 106. As in previous embodiments, the flow rate regulator 582 may receive control signals from a controller (not shown) via wired or wireless transmission.

Figure 6:
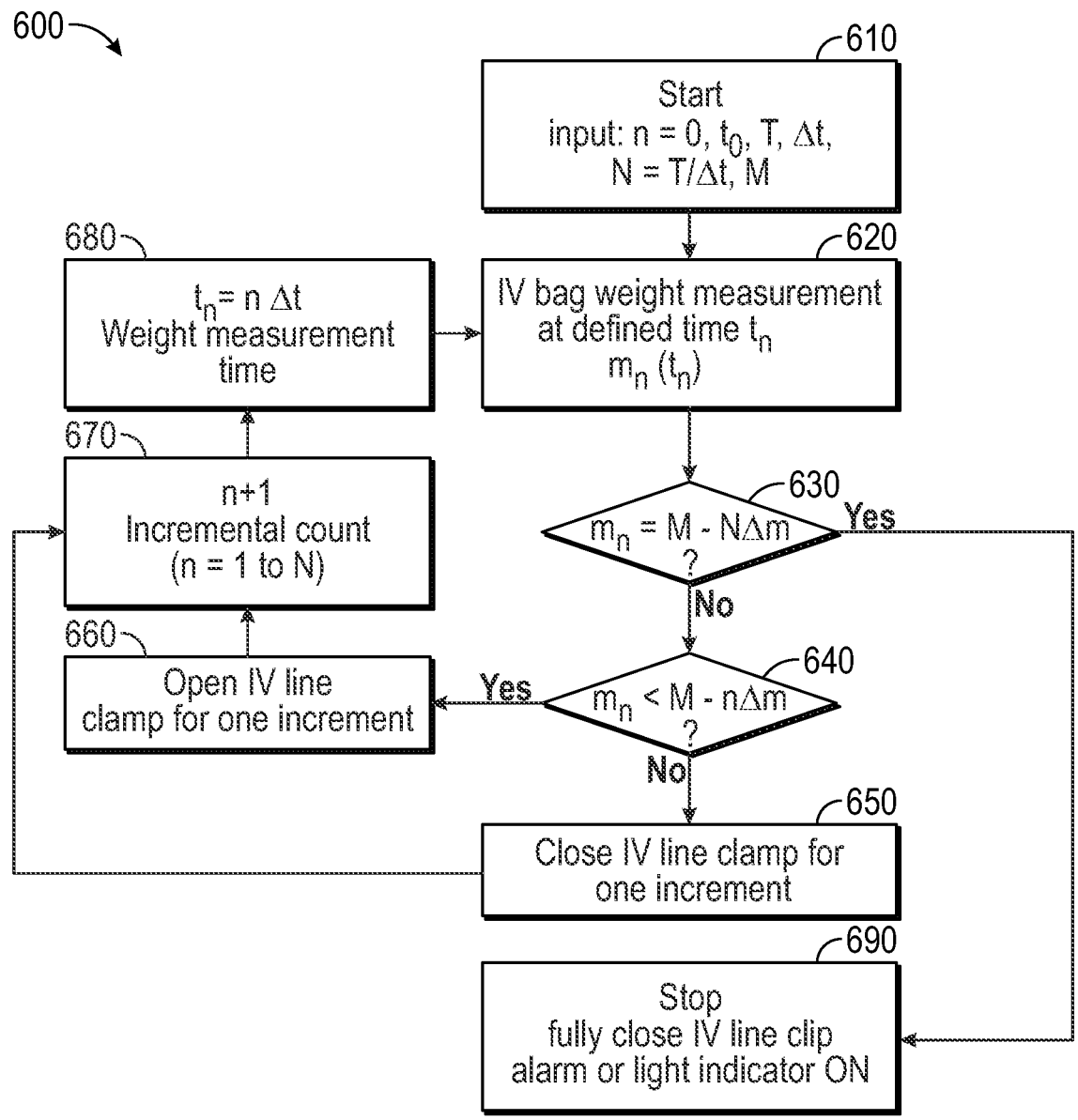
FIG. 6 is a flowchart diagram illustrating a method of controlling the flow rate of liquid delivered with an intravenous delivery system, according to an alternative embodiment.

Referring to FIG. 6, a flowchart diagram illustrates a method 600 of controlling the flow rate of liquid delivered with an intravenous delivery system, according to an alternative embodiment. The method 600 may be applicable particularly to embodiments in which the flow rate regulator 182 has an open state and a closed state, without any partially open state in which flow of the liquid 122 is permitted, but restricted. Further, the method 600 may apply particularly to gravimetric flow rate measurement, using a weight measurement (as described previously) of a liquid source 102 in the form of an IV bag. In the flowchart, M is the total mass of the liquid 122 to be delivered from the IV bag, T is the total time over which M is to be delivered, $\Delta t$ is the time increment at which the weight of the IV bag will be measured, $$N = \frac{T}{\Delta t}$$

is the total number of time increments, $$\Delta m = \frac{M}{N}$$

is the mass increment that corresponds to the time increment, n is the increment count, $m_n$ is the IV bag weight measurement at a given time increment, and $t_n$ is the time at which the weight of the IV bag is measured.

As shown, the method 600 may start 610 with receipt of input that provides the necessary starting values, as shown. Some of these values, such as M and T, may be provided by a clinician based on the needs of the patient.

In a step 620, the IV bag weight may be measured at a time $t_n$. Then, in a query 630, a determination may be made as to whether the desired total mass M of the liquid 122 has been delivered to the patient. If so, the method 600 may stop 690, and the flow rate regulator 182 may be fully closed to prevent further delivery of the liquid 122 to the patient. An alarm, light, or other indicator (for example, on the controller 184) may be activated to indicate, to a clinician, that delivery of the liquid 122 is complete.

If the desired total mass M of the liquid 122 has not yet been delivered to the patient, the method 600 may continue to a step 640 in which a determination is made as to whether the flow rate of the liquid 122 to the patient is too low to achieve delivery of the desired total mass M of the liquid 122 within the time T. If not, the method 600 may proceed to a step 650 in which the flow rate regulator 182 is actuated to stop flow of the liquid 122 to the patient for a single time increment Δt. If so, the method 600 may proceed to a step 660 in which the flow rate regulator 182 is actuated to allow flow of the liquid 122 to the patient for a single time increment Δt.

After performance of either the step 650 or the step 660, the method 600 may proceed to a step 670 in which the increment count n is incremented to n+1. Then, in a step 680, once sufficient time has passed, a determination may be made that it is time for the weight of the IV bag to be measured again. The method 600 may then proceed to the step 620. The method 600 may thus iterate until the query 630 is satisfied, and delivery of the liquid 122 is complete.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An intravenous delivery system for controlling flow of a liquid to a patient, the system comprising:
a drip unit comprising a drip chamber and an orifice that delivers drops of the liquid from a liquid source to the drip chamber via gravity feed;
a flow rate sensor comprising an interior cavity encasing a lower portion of the drip unit, wherein the flow rate sensor further comprises a first arm and a second arm, wherein the first arm and the second arm extend upward toward a top of the drip unit, wherein the first arm comprises a light source that emits light that passes through the drip chamber, wherein the second arm comprises a light sensor that detects the light, wherein the flow rate sensor is configured to:
measure a flow rate of the liquid through the intravenous delivery system; and
generate a flow rate signal indicative of the flow rate;
a controller that:
receives the flow rate signal;
compares the flow rate with a desired flow rate to determine that the flow rate is different from the desired flow rate; and
in response to determining that the flow rate is different from the desired flow rate, transmits a control signal; and
a flow rate regulator that:
receives the control signal; and
in response to receipt of the control signal, modifies the flow rate to bring the flow rate closer to the desired flow rate.

2. The system of claim 1, wherein the flow rate sensor, the controller, and the flow rate regulator all operate iteratively throughout a plurality of time increments such that, in each of the plurality of time increments, the flow rate sensor measures the flow rate and generates the flow rate signal, and the controller receives the flow rate signal and compares the flow rate with the desired flow rate;
wherein the controller determines that the flow rate is different from the desired flow rate by determining that the flow rate is greater than the desired flow rate;
wherein, in response to receipt of the control signal, the flow rate regulator:
modifies the flow rate by moving from an open state that permits the liquid to flow through the intravenous delivery system, to a closed state that substantially prevents the liquid from flowing through the intravenous delivery system; and
remains in the closed state for a predetermined number of the time increments.

3. The system of claim 1, wherein the flow rate sensor, the controller, and the flow rate regulator all operate iteratively throughout a plurality of time increments such that, in each of the plurality of time increments, the flow rate sensor measures the flow rate and generates the flow rate signal, and the controller receives the flow rate signal and compares the flow rate with the desired flow rate;
wherein the controller determines that the flow rate is different from the desired flow rate by determining that the flow rate is less than the desired flow rate;
wherein, in response to receipt of the control signal, the flow rate regulator:
modifies the flow rate by moving from a closed state that substantially prevents the liquid from flowing through the intravenous delivery system, to an open state in that permits the liquid to flow through the intravenous delivery system; and
remains in the open state for a predetermined number of the time increments.

4. The system of claim 1, wherein the controller determines that the flow rate is different from the desired flow rate by determining that the flow rate is greater than the desired flow rate by a differential flow rate;
wherein, in response to receipt of the control signal, the flow rate regulator moves, in proportion to the differential flow rate, to a less open state that permits the liquid to flow through the intravenous delivery system at a modified flow rate smaller than the flow rate.

5. The system of claim 1, wherein the controller determines that the flow rate is different from the desired flow rate by determining that the flow rate is less than the desired flow rate by a differential flow rate;
wherein, in response to receipt of the control signal, the flow rate regulator moves, in proportion to the differential flow rate, to a more open state that permits the liquid to flow through the intravenous delivery system at a modified flow rate greater than the flow rate.

6. The system of claim 1, further comprising a retention unit having a main body and an extension, further comprising a tubing that conveys the liquid from the drip unit, wherein the tubing comprises a first end connected to the main body, wherein the tubing comprises a second end connected to the extension, wherein the controller is incorporated into a computing device comprising a display screen and a user input device, wherein the controller is secured to the main body, wherein the controller further:
- receives the desired flow rate from a user via the user input device; and
- initiates display of the flow rate on the display screen.

7. The system of claim 1, further comprising the drip unit;
- wherein the drip unit comprises a key feature indicative of an orifice size of the orifice;
- wherein the first arm of the flow rate sensor comprises a key feature receiver that receives the key feature in response to securement of the flow rate sensor to the drip unit;
- wherein the flow rate sensor uses the orifice size to determine a volume of the liquid in each of the drops to facilitate measurement of the flow rate.

8. The system of claim 1, wherein the intravenous delivery system comprises tubing that conveys the liquid, wherein the flow rate regulator comprises:
- an opposing member positioned adjacent to the tubing;
- a cam member positioned on an opposite side of the tubing from the opposing member; and
- a motor that rotates the cam member about an axis;
- wherein the cam member comprises a variable radius curved rim that, in response to rotation of the cam member about the axis, cooperates with the opposing member to exert a varying degree of compression on the tubing to modify the flow rate.

9. The system of claim 1, wherein the intravenous delivery system comprises tubing that conveys the liquid, wherein the flow rate regulator comprises:
- a fixture comprising a slot oriented nonparallel and nonperpendicular to the tubing;
- a pinching member positioned in the slot; and
- a motor that urges the pinching member to move along the slot such that the pinching member exerts a varying degree of compression on the tubing to modify the flow rate.

10. The system of claim 1, further comprising:
- tubing comprising:
  - a first end connected to the drip unit to receive the liquid from the drip unit via gravity feed; and
  - a second end; and
- an intravenous access unit connected to the second end of the tubing, wherein the intravenous access unit is configured to receive the liquid from the second end via gravity feed and deliver the liquid intravenously to a patient.

11. A method for controlling flow of a liquid to a patient through use of an intravenous delivery system, the method comprising:
- with a flow rate sensor coupled to a drip unit:
  - measuring a flow rate of the liquid through the intravenous delivery system; and
  - generating a flow rate signal indicative of the flow rate;
- with a controller:
  - receiving the flow rate signal;
  - comparing the flow rate with a desired flow rate to determine that the flow rate is different from the desired flow rate; and
  - in response to determining that the flow rate is different from the desired flow rate, transmitting a control signal, wherein the drip unit comprises a drip chamber and an orifice that delivers drops of the liquid from a liquid source to the drip chamber via gravity feed wherein the flow rate sensor comprises an interior cavity encasing a lower portion of the drip unit, wherein the flow rate sensor further comprises a first arm and a second arm, wherein the first arm and the second arm extend upward toward a top of the drip unit, wherein the first arm comprises a light source that emits light that passes through the drip chamber, wherein the second arm comprises a light sensor that detects the light; and with a flow rate regulator:
    - receiving the control signal; and
    - in response to receipt of the control signal, modifying the flow rate to bring the flow rate closer to the desired flow rate.

12. The method of claim 11, wherein measuring the flow rate, generating the flow rate signal, receiving the flow rate signal, and comparing the flow rate with the desired flow rate are all carried out iteratively throughout a plurality of time increments such that, in each of the plurality of time increments, the flow rate is measured, the flow rate signal is generated, the flow rate signal is received, and the flow rate is compared with the desired flow rate;
- wherein modifying the flow rate comprises moving the flow rate regulator from one of an open state that permits the liquid to flow through the intravenous delivery system, and a closed state that substantially prevents the liquid from flowing through the intravenous delivery system, to the other of the open state and the closed state;
- wherein the method further comprises causing the flow rate regulator to remain in the other of the open state and the closed state for a predetermined number of the time increments.

13. The method of claim 11, wherein determining that the flow rate is different from the desired flow rate comprises determining that the flow rate differs from the desired flow rate by a differential flow rate;
- wherein modifying the flow rate comprises moving the flow rate regulator in proportion to the differential flow rate to perform one of increasing the flow rate and decreasing the flow rate.

14. The method of claim 11, wherein the controller is incorporated into a computing device comprising a display screen and a user input device, the method further comprising:
- via the user input device, and prior to comparing the flow rate with the desired flow rate, receiving the desired flow rate from a user; and
- via the display screen and after generating the flow rate signal, initiating display of the flow rate.

15. A system for controlling flow of a liquid to a patient, the system comprising:
- a drip unit comprising a drip chamber and an orifice that delivers drops of the liquid from a liquid source to the drip chamber via gravity feed;
- a flow rate sensor coupled to the drip unit, wherein the flow rate sensor comprises an interior cavity encasing a lower portion of the drip unit, wherein the flow rate sensor further comprises a first arm and a second arm, wherein the first arm and the second arm extend upward toward a top of the drip unit, wherein the first arm comprises a light source that emits light that passes through the drip chamber, wherein the second arm comprises a light sensor that detects the light, wherein the flow rate sensor is configured to—wherein the flow rate sensor:
  measures a flow rate of the liquid through the drip chamber; and
  generates a flow rate signal indicative of the flow rate;
a controller that:
  receives the flow rate signal;
  compares the flow rate with a desired flow rate to determine that the flow rate is different from the desired flow rate; and
  in response to determining that the flow rate is different from the desired flow rate, transmits a control signal;
tubing comprising:
  a first end connected to the drip unit to receive the liquid from the drip unit via gravity feed; and
  a second end;
a flow rate regulator coupled to the tubing, wherein the flow rate regulator:
  receives the control signal; and
  in response to receipt of the control signal, adjusts a level of compression applied to the tubing to modify the flow rate to bring the flow rate closer to the desired flow rate; and
an intravenous access unit connected to the second end of the tubing, wherein the intravenous access unit is configured to receive the liquid from the second end via gravity feed and deliver the liquid intravenously to a patient.

16. The system of claim 15, wherein the controller is incorporated into a computing device comprising a display screen and a user input device, wherein the controller further:
  receives the desired flow rate from a user via the user input device; and
  initiates display of the flow rate on the display screen.

\* \* \* \* \*